United States Patent
Matsuda

(10) Patent No.: US 9,976,992 B2
(45) Date of Patent: May 22, 2018

(54) ULTRASONIC DEVICE, METHOD FOR MANUFACTURING THE SAME, PROBE, AND ELECTRONIC APPARATUS

(71) Applicant: SEIKO EPSON CORPORATION, Tokyo (JP)

(72) Inventor: Hiroshi Matsuda, Gifu (JP)

(73) Assignee: Seiko Epson Corporation, Tokyo (JP)

( * ) Notice: Subject to any disclaimer, the term of this patent is extended or adjusted under 35 U.S.C. 154(b) by 313 days.

(21) Appl. No.: 14/807,108

(22) Filed: Jul. 23, 2015

(65) Prior Publication Data

US 2016/0033454 A1 Feb. 4, 2016

(30) Foreign Application Priority Data

Jul. 31, 2014 (JP) ................... 2014-156708

(51) Int. Cl.
*G01N 29/24* (2006.01)
*H01L 41/08* (2006.01)
*B06B 1/06* (2006.01)

(52) U.S. Cl.
CPC ....... *G01N 29/2437* (2013.01); *B06B 1/0622* (2013.01); *H01L 41/08* (2013.01)

(58) Field of Classification Search
CPC .......................... G01N 29/2437; B06B 1/0622; B06B 1/0607; B06B 1/0629; H01L 41/08; H01L 41/0805; H01L 41/081
USPC ........... 73/632, 641, 642, 649; 310/334, 322
See application file for complete search history.

(56) References Cited

U.S. PATENT DOCUMENTS

| 6,584,660 | B1 | 7/2003 | Shimogawa et al. |
| 9,197,331 | B2 * | 11/2015 | Nishiwaki ............. H04B 11/00 |
| 9,818,929 | B2 * | 11/2017 | Kiyose ................. A61B 8/4427 |
| 2013/0223191 | A1 | 8/2013 | Nakamura et al. |
| 2013/0338502 | A1 * | 12/2013 | Onishi ................. A61B 8/4494 600/443 |
| 2015/0141827 | A1 * | 5/2015 | Kiyose ................. A61B 8/4427 310/322 |
| 2015/0298172 | A1 | 10/2015 | Nakamura et al. |
| 2017/0136497 | A1 | 5/2017 | Nakamura et al. |

FOREIGN PATENT DOCUMENTS

| JP | 2001-322271 A | 11/2001 |
| JP | 2003-008096 A | 1/2003 |
| JP | 2013-175879 A | 9/2013 |

* cited by examiner

*Primary Examiner* — Manish S Shah
*Assistant Examiner* — Suman K Nath

(57) ABSTRACT

An ultrasonic device that has high accuracy with respect to frequency and sensitivity and that can achieve a reduction of crosstalk is provided. A substrate of an ultrasonic device has a first surface and a second surface on a side opposite to the first surface, and has a first opening and a second opening that are separated from each other by a wall portion. A first vibration film and a second vibration film that close the first opening and the second opening, respectively, are disposed on the first surface of the substrate. A first piezoelectric element and a second piezoelectric element are provided on the first vibration film and the second vibration film, respectively. A recess that opens in the second surface of the substrate is demarcated in the wall portion.

12 Claims, 12 Drawing Sheets

— 1 —

ULTRASONIC DEVICE, METHOD FOR MANUFACTURING THE SAME, PROBE, AND ELECTRONIC APPARATUS

BACKGROUND

1. Technical Field

The present invention relates to an ultrasonic device, a method for manufacturing the same, and a probe, an electronic apparatus, an ultrasonic imaging apparatus, and the like using the same.

2. Related Art

Ultrasonic devices for use in, for example, ultrasonic diagnostic apparatuses are commonly known. The structure of such an ultrasonic device is similar to the structure of a piezoelectric device. That is to say, openings are formed in an array in a substrate, where the openings are separated from one another by wall portions, and the individual openings are closed by respective vibration films. Piezoelectric elements are disposed on the respective vibration films.

In a piezoelectric device disclosed in JP-A-2003-8096, in order to increase displacement, that is, to obtain a large amplitude, low-stiffness portions are established by forming grooves near fixed ends of vibration films, and a slight variation in size, depth, and position of the grooves may affect the frequency and the sensitivity of ultrasonic elements. For this reason, even though crosstalk is reduced, the accuracy of the ultrasonic device is low.

SUMMARY

According to at least one aspect of the invention, it is possible to provide an ultrasonic device that has high accuracy with respect to frequency and sensitivity and that can realize a reduction of crosstalk.

(1) An aspect of the invention is directed to an ultrasonic device including a substrate having a first surface and a second surface on a side opposite to the first surface and having a first opening and a second opening that are separated from each other by a first wall portion, a first vibration film and a second vibration film that are disposed on the first surface of the substrate and that close the first opening and the second opening, respectively, and a first piezoelectric element and a second piezoelectric element that are provided on the first vibration film and the second vibration film, respectively, wherein a first recess that opens in the second surface is formed in the first wall portion.

The first vibration film and the second vibration film vibrate. Since the first recess is formed in the first wall portion, vibration propagating through the first wall portion is reflected by the space in the first recess. Therefore, propagation of vibration between the first vibration film and the second vibration film that are adjacent to each other is suppressed. Thus, crosstalk between the first vibration film and the second vibration film is reduced. At this time, since the first recess does not pass through the substrate and does not reach the first surface, no groove or depression is formed in a region of the first surface between the first vibration film and the second vibration film. The stiffness of supporting points of the first vibration film and the second vibration film is maintained. The vibration characteristics of the first vibration film and the second vibration film are maintained. Variation in the vibration characteristics is suppressed.

(2) It is also possible that the ultrasonic device includes a first interconnect that is connected to the first piezoelectric element and a second interconnect that is isolated from the first interconnect by an insulator and that is connected to the second piezoelectric element. Signals are separately transmitted through the first interconnect and the second interconnect. The first interconnect and the second interconnect individually form a channel. Thus, a space is disposed at least between different channels. Crosstalk between the channels is reduced.

(3) The substrate can have a third opening that is separated from the first opening by the second wall portion and a fourth opening that is separated from the second opening by a third wall portion and separated from the third opening by a fourth wall portion. The ultrasonic device can further include a third vibration film and a fourth vibration film that are disposed on the first surface of the substrate and that close the third opening and the fourth opening, respectively, and a third piezoelectric element and a fourth piezoelectric element that are provided on the third vibration film and the fourth vibration film, respectively. At this time, it is preferable that the third piezoelectric element is connected to the first interconnect, the fourth piezoelectric element is connected to the second interconnect, and a second recess that opens in the second surface is formed in the fourth wall portion. The ultrasonic device has a plurality of openings for each channel. The openings are closed by respective vibration films, and piezoelectric elements are provided on the respective vibration films. That is to say, the first and third openings, the first and third vibration films, and the first and third piezoelectric elements form a single channel. The first interconnect is connected commonly to the first piezoelectric element and the third piezoelectric element. Similarly, the second and fourth openings, the second and fourth vibration films, and the second and fourth piezoelectric elements form a single channel. The second interconnect is connected commonly to the second piezoelectric element and the fourth piezoelectric element. Thus, signals are enhanced on a channel-by-channel basis.

(4) It is also possible that the first recess and the second recess in a plan view when viewed in a thickness direction of the substrate are groove-shaped, extending in an extending direction of a row in which the first opening and the third opening are arranged. The groove shape makes it possible to efficiently block propagation of vibration between the row in which the first opening and the second opening are arranged and the row in which the third opening and the fourth opening are arranged.

(5) It is preferable that the first recess and the second recess have a depth that is smaller than depths of all of the first to fourth openings. Thus, the first recess and the second recess are located away from the first surface of the substrate. The stiffness of the substrate can be maintained.

(6) It is preferable that a width of the first recess and a width of the second recess in a direction orthogonal to the extending direction of the row in which the first opening and the third opening are arranged are smaller than widths of all of the first to fourth openings. The first and second recesses and the first to fourth openings can be formed simultaneously by etching. It is more difficult for an etching solution to enter the first and second recesses than to enter the first to fourth openings. As a result, if the first and second recesses are formed to have a narrow width, even when a traditional method for forming the first to fourth openings is followed, the grooves that are shallower than the first to fourth openings can be formed by simply making a change in patterning.

(7) It is preferable that with respect to the extending direction, the first recess and the second recess have a length that is smaller than lengths of all of the first to fourth openings. A higher stiffness of the substrate can be secured while reducing crosstalk.

(8) It is also possible that a third recess that opens in the second surface is formed in the second wall portion, and a fourth recess that opens in the second surface is formed in the third wall portion. The third recess blocks propagation of vibration between the first opening and the third opening, and the fourth recess blocks propagation of vibration between the second opening and the fourth opening. Thus, crosstalk between the first opening and the third opening and between the second opening and the fourth opening can be reduced.

(9) It is preferable that the third recess and the fourth recess are groove-shaped, respectively extending in a direction that intersects the first interconnect that connects the first piezoelectric element and the third piezoelectric element and a direction that intersects the second interconnect that connects the second piezoelectric element and the fourth piezoelectric element. The groove shape makes it possible to efficiently block propagation of vibration between the first opening and the third opening and between the second opening and the fourth opening.

(10) The ultrasonic device can be used in a state in which it is incorporated into a probe. At this time, it is sufficient if the probe includes the ultrasonic device and a housing that supports the ultrasonic device.

(11) The ultrasonic device can be used in a state in which it is incorporated into an electronic apparatus. At this time, it is sufficient if the electronic apparatus includes the ultrasonic device and a processor that is connected to the ultrasonic device and that processes an output from the ultrasonic device.

(12) The ultrasonic device can be used in a state in which it is incorporated into an ultrasonic imaging apparatus. At this time, it is sufficient if the ultrasonic imaging apparatus includes the ultrasonic device and a display device that displays an image generated based on an output from the ultrasonic device.

(13) Another aspect of the invention is directed to a method for manufacturing an ultrasonic device, the method including forming a coating film on a first surface of a substrate that has the first surface and a second surface on a side opposite to the first surface; forming a first piezoelectric element and a second piezoelectric element at predetermined positions on the coating film; forming a resist film that demarcates a first cavity and a second cavity at positions on the second surface of the substrate respectively corresponding to the first piezoelectric element and the second piezoelectric element, the first cavity and the second cavity respectively corresponding to outlines of a first vibration film and a second vibration film, and that demarcates a third cavity located between the first cavity and the second cavity; and subjecting the second surface of the substrate to an etching process, thereby forming a first opening and a second opening that reach the coating film and a recess in a wall portion that separates the first opening and the second opening from each other, where the recess opens in the second surface and does not reach the coating film.

The ultrasonic device is manufactured in this manner. Formation of the recess and formation of the first opening and the second opening can be performed by the same etching process. Therefore, merely changing the patterning of the resist film makes it possible to form the recess without increasing the manufacturing steps.

(14) It is desirable that the third cavity has a width that is smaller than widths of the first cavity and the second cavity.

During the etching process, it is difficult for an etching solution to enter the space, which does not pass through the substrate, from the third cavity than to enter the first opening and the second opening. As a result, even when a traditional method for forming the first opening and the second opening is followed, the space that is shallower than the first opening and the second opening and that does not pass through the substrate can be formed by simply making a change in patterning.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following describes embodiments of the invention with reference to the attached drawings. It should be noted that the embodiments to be described hereinafter are not intended to unduly limit the scope of the invention defined by the claims and that not all of the configurations to be described in the embodiments are necessarily essential as the means for achieving the invention.

(1) Overall Configuration of Ultrasonic Diagnostic Apparatus

Figure 1:
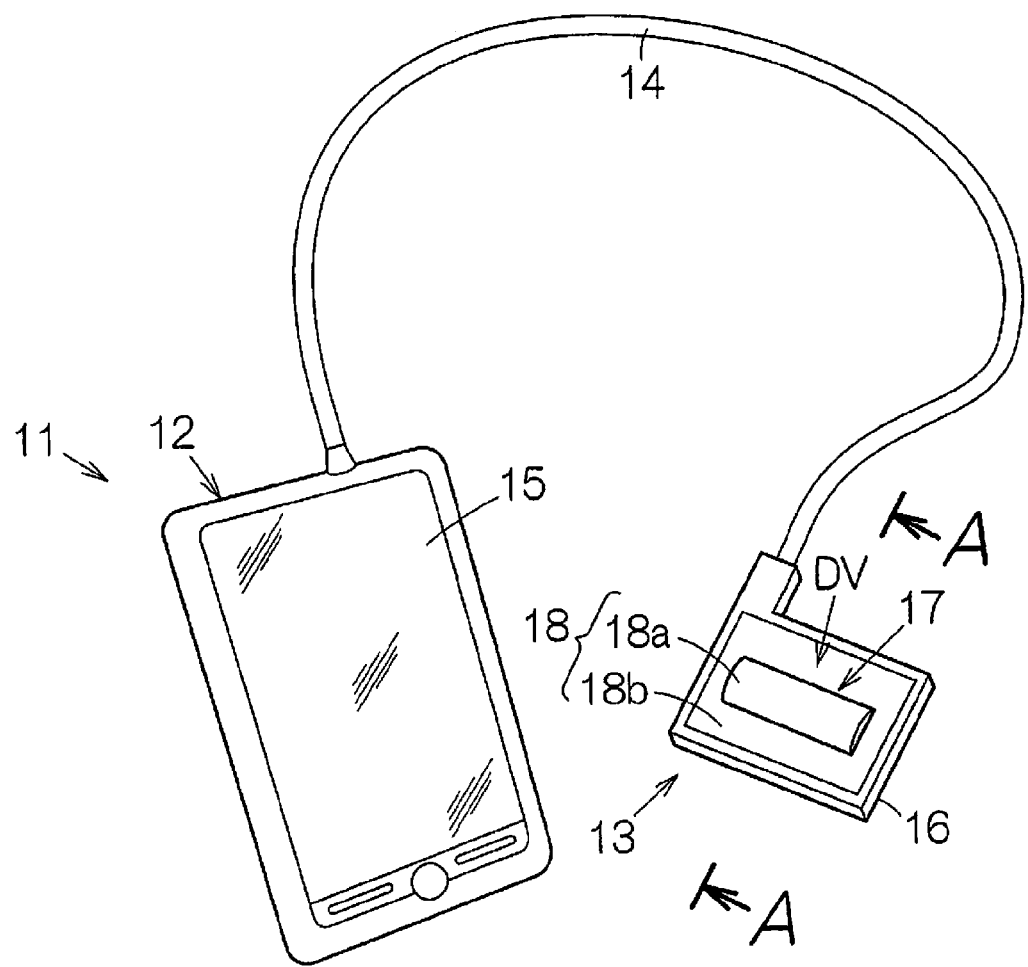
FIG. 1 is an external view schematically showing a specific example, that is, an ultrasonic diagnostic apparatus, of an electronic apparatus according to an embodiment.

FIG. 1 schematically shows the configuration of a specific example, that is, an ultrasonic diagnostic apparatus (ultrasonic imaging apparatus) 11, of an electronic apparatus according to an embodiment of the invention. The ultrasonic diagnostic apparatus 11 includes a device terminal (processing unit) 12 and an ultrasonic probe (probe) 13. The device terminal 12 and the ultrasonic probe 13 are connected to each other via a cable 14. Electric signals are transmitted through the cable 14 between the device terminal 12 and the ultrasonic probe 13. A display panel (display device) 15 is incorporated into the device terminal 12. A screen of the display panel 15 is exposed at a surface of the device terminal 12. In the device terminal 12, an image is generated based on ultrasonic waves detected by the ultrasonic probe 13. The imaged detection result is displayed on the screen of the display panel 15.

The ultrasonic probe 13 has a housing 16. An ultrasonic device unit DV is fitted in the housing 16. The ultrasonic device unit DV includes an ultrasonic device 17. The ultrasonic device 17 includes an acoustic lens 18. A partial cylindrical surface 18a is formed on an outer surface of the acoustic lens 18. The partial cylindrical surface 18a is surrounded by a flat plate portion 18b. The entire outer perimeter of the flat plate portion 18b is continuously joined to the housing 16. Thus, the flat plate portion 18b functions as a portion of the housing. The acoustic lens 18 may be formed of, for example, a silicone resin. The acoustic lens 18 has an acoustic impedance that is similar to the acoustic impedance of a living body. The ultrasonic device 17 outputs ultrasonic waves from its surface and receives reflected waves of the ultrasonic waves.

(2) Ultrasonic Device According to First Embodiment

Figure 2:
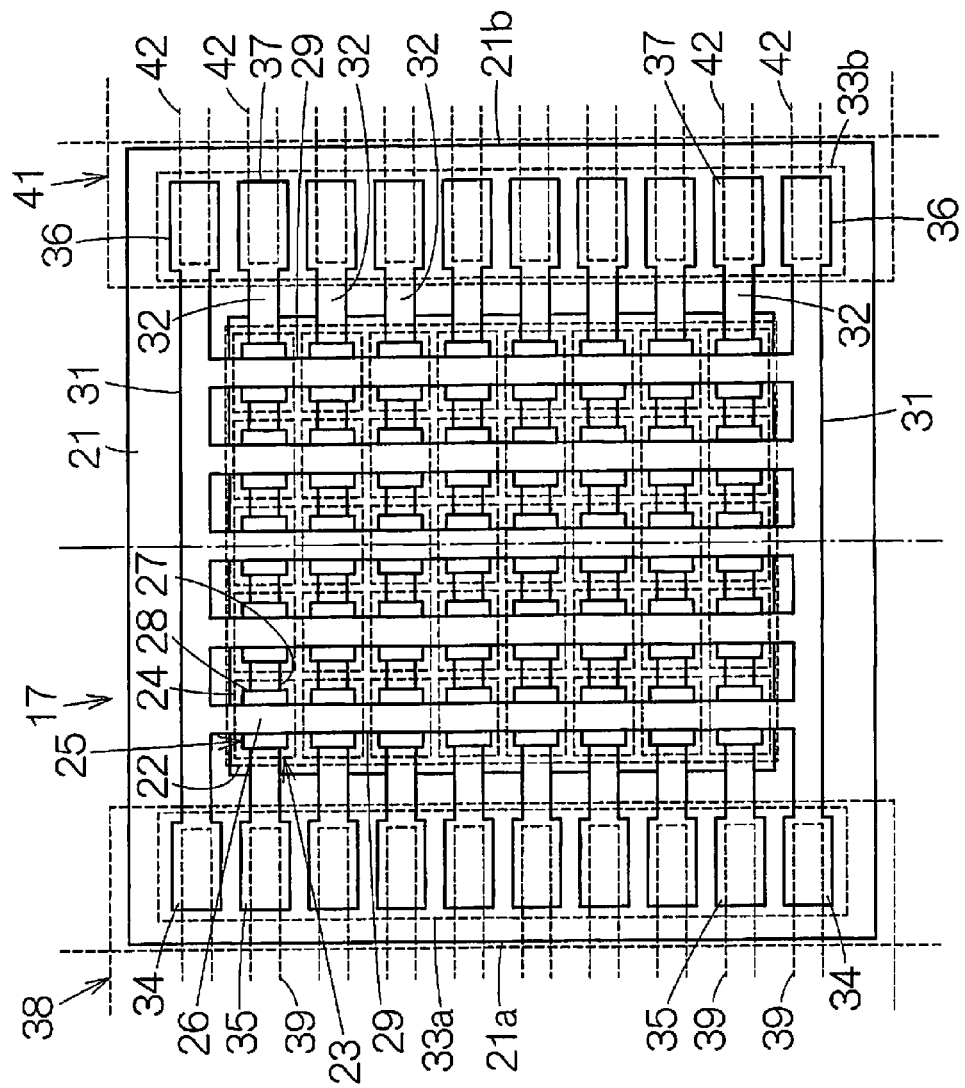
FIG. 2 is an enlarged plan view of an ultrasonic device according to a first embodiment.

FIG. 2 schematically shows a plan view of the ultrasonic device 17. The ultrasonic device 17 includes a base 21. An element array 22 is formed on a surface (first surface) of the base 21. The element array 22 is constituted by an arrangement of thin-film ultrasonic transducer elements (hereinafter referred to as "elements") 23 that are arranged in an array. The arrangement is in the form of a matrix having a plurality of columns and a plurality of rows. The arrangement may also be established as a staggered arrangement. In a staggered arrangement, a group of elements 23 in each even row can be displaced relative to a group of elements 23 in each odd row by one-half of the column pitch. Either the number of elements in each odd row or the number of elements in each even row may be smaller than the other by one.

Each element 23 includes a vibration film 24. In FIG. 2, the outline of the vibration film 24 when viewed from above in a direction perpendicular to the film surface of the vibration film 24 (when viewed from above in a thickness direction of a substrate) is shown by dashed lines. A piezoelectric element 25 is formed on the vibration film 24. The piezoelectric element 25 is constituted by a top electrode 26, a bottom electrode 27, and a piezoelectric film 28. In each element 23, the piezoelectric film 28 is sandwiched between the top electrode 26 and the bottom electrode 27. The bottom electrode 27, the piezoelectric film 28, and the top electrode 26 are laid one on top of another in that order. The ultrasonic device 17 is configured as a single ultrasonic transducer element chip (substrate).

A plurality of first electric conductors 29 are formed on the surface of the base 21. The first electric conductors 29 extend parallel to one another in a column direction of the arrangement. One first electric conductor 29 is assigned to corresponding one column of elements 23. One first electric conductor 29 is connected commonly to the piezoelectric films 28 of the respective elements 23 that are lined up in the column direction of the arrangement. The first electric conductor 29 forms the top electrodes 26 for the respective elements 23. Both ends of the first electric conductor 29 are respectively connected to a pair of extraction interconnects 31. The extraction interconnects 31 extend parallel to each other in a row direction of the arrangement. Accordingly, all of the first electric conductors 29 have the same length. Thus, the top electrodes 26 are connected commonly to the elements 23 of the entire matrix. The first electric conductors 29 can be formed of, for example, iridium (Ir). However, other electrically conductive materials may also be used for the first electric conductors 29.

A plurality of second electric conductors 32 are formed on the surface of the base 21. The second electric conductors 32 extend parallel to one another in the row direction of the arrangement. One second electric conductor 32 is assigned to corresponding one row of elements 23. One second electric conductor 32 is connected commonly to the piezoelectric films 28 of the respective elements 23 that are lined up in the row direction of the arrangement. The second electric conductor 32 forms the bottom electrodes 27 for the respective elements 23. For example, a laminated film composed of titanium (Ti), iridium (Ir), platinum (Pt), and titanium (Ti) can be used for the second electric conductors 32. However, other electrically conductive materials may also be used for the second electric conductors 32.

Energization of the elements 23 is switched on a row-by-row basis. A linear scan and a sector scan can be achieved in accordance with this switching of energization. Since the elements 23 in a single row simultaneously output ultrasonic waves, the number of elements in a single row, that is, the number of columns of the arrangement can be determined in accordance with the output level of ultrasonic waves. The number of columns can be set at, for example, about 10 to 15. In FIG. 2, some columns are not shown, and only five columns are shown. The number of rows of the arrangement can be determined in accordance with the extent of the scan range. The number of rows can be set at, for example, 128 or 256. In FIG. 2, some rows are not shown, and only eight rows are shown. The functions of the top electrodes 26 and the bottom electrodes 27 may be reversed. That is to say, it is also possible that while the bottom electrodes are connected commonly to the elements 23 of the entire matrix, the top electrodes are connected commonly to the elements 23 in each row of the arrangement.

The outline of the base 21 has a first side 21a and a second side 21b that are defined by a pair of mutually parallel straight lines and that oppose each other. A first terminal array 33a in a single line is disposed between the first side 21a and the outline of the element array 22. A second terminal array 33b in a single line is disposed between the second side 21b and the outline of the element array 22. The first terminal array 33a can form a single line parallel to the first side 21a. The second terminal array 33b can form a single line parallel to the second side 21b. The first terminal array 33a is constituted by a pair of top electrode terminals 34 and a plurality of bottom electrode terminals 35. Similarly, the second terminal array 33b is constituted by a pair of top electrode terminals 36 and a plurality of bottom electrode terminals 37. One top electrode terminal 34 and one top electrode terminal 36 are respectively connected to the two ends of a single extraction interconnect 31. It is sufficient if the extraction interconnects 31 and the top electrode terminals 34 and 36 are formed plane-symmetrically with respect to a perpendicular plane that bisects the element array 22. One bottom electrode terminal 35 and one bottom electrode terminal 37 are respectively connected to the two ends of a single second electric conductor 32. It is sufficient if the second electric conductors 32 and the bottom electrode terminals 35 and 37 are formed plane-symmetrically with respect to the perpendicular plane that bisects the element array 22. Here, the base 21 is formed to have a rectangular outline. The outline of the base 21 may also be square or may be trapezoidal.

A first flexible printed wiring board (hereinafter referred to as "first wiring board") 38 is connected to the base 21. The first wiring board 38 covers the first terminal array 33a. Electrically conductive lines, namely, first signal lines 39 are formed at one end of the first wiring board 38, respectively corresponding to the top electrode terminals 34 and the bottom electrode terminals 35. The first signal lines 39 are respectively opposed to the top electrode terminals 34 and the bottom electrode terminals 35 and respectively joined thereto. Similarly, a second flexible printed wiring board (hereinafter referred to as "second wiring board") 41 covers the base 21. The second wiring board 41 covers the second terminal array 33b. Electrically conductive lines, namely, second signal lines 42 are formed at one end of the second wiring board 41, respectively corresponding to the top electrode terminals 36 and the bottom electrode terminals 37. The second signal lines 42 are respectively opposed to the top electrode terminals 36 and the bottom electrode terminals 37 and respectively joined thereto.

Figure 3:
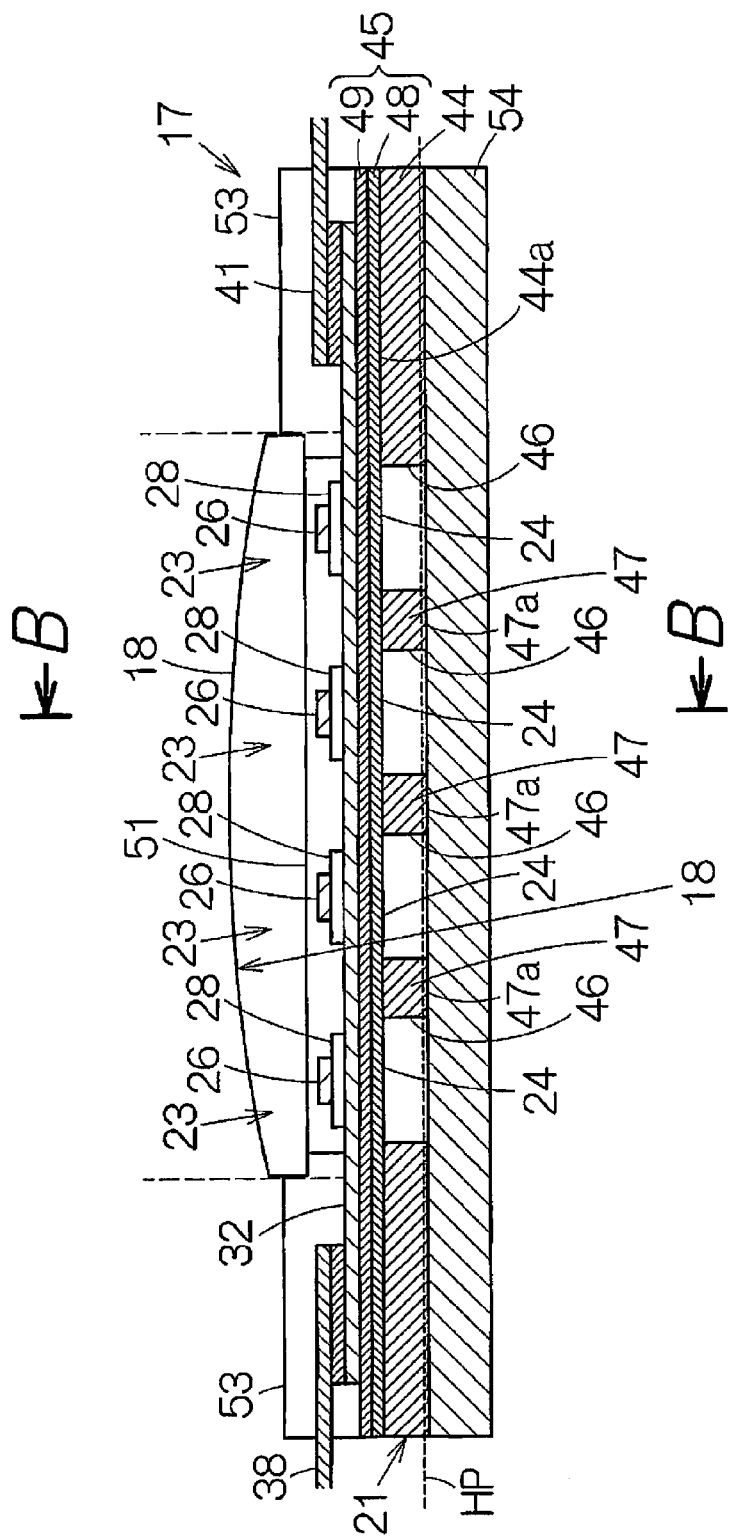
FIG. 3 is a partial cross-sectional view of an ultrasonic device unit according to the embodiment taken along line A-A in FIG. 1.

As shown in FIG. 3, the base 21 includes a substrate 44 and a coating film 45. The coating film 45 is laminated over the entire surface (first surface) 44a of the substrate 44. In the substrate 44, an opening 46 is formed for each of the elements 23. The openings 46 define respective spaces that are hollowed out from a back surface (second surface) 44b of the substrate 44 and that pass through the substrate 44. The openings 46 are arranged in an array in the substrate 44. The outline of a region where the openings 46 are arranged corresponds to the outline of the element array 22. The substrate 44 can be formed of, for example, a silicon substrate.

A partitioning wall (wall portion) 47 is disposed between every two adjacent openings 46. Adjacent openings 46 are separated from each other by the partitioning walls 47. The wall thickness of the partitioning walls 47 corresponds to the spacing between the openings 46. Each partitioning wall 47 defines two wall surfaces within planes that extend parallel to each other. The wall thickness corresponds to the distance between the two wall surfaces. That is to say, the wall thickness can be defined by the length of a normal line that extends between the wall surfaces orthogonally to the wall surfaces.

The coating film 45 is composed of a silicon oxide ($SiO_2$) layer 48 that is laminated on the surface of the substrate 44 and a zirconium oxide ($ZrO_2$) layer 49 that is laminated on a surface of the silicon oxide layer 48. The coating film 45 is in contact with the openings 46. Thus, portions of the coating film 45 that correspond to the respective outlines of the openings 46 form the vibration films 24. The vibration films 24 refer to those portions of the coating film 45 that face the respective openings 46 and that can thus vibrate in the thickness direction of the substrate 44. The film thickness of the silicon oxide layer 48 can be determined based on resonance frequency.

The bottom electrode 27, the piezoelectric film 28, and the top electrode 26 are sequentially laminated on the surface of each vibration film 24. The piezoelectric film 28 can be formed of, for example, lead zirconate titanate (PZT). Other piezoelectric materials may also be used for the piezoelectric film 28. Here, the piezoelectric film 28 under the first electric conductor 29 completely covers the second electric conductor 32. The piezoelectric film 28 can serve to avoid short-circuiting between the first electric conductor 29 and the second electric conductor 32.

An acoustic matching layer 51 is laminated over the surface of the base 21. The acoustic matching layer 51 covers the element array 22. The film thickness of the acoustic matching layer 51 is determined in accordance with the resonance frequency of the vibration films 24. For example, a silicone resin film can be used for the acoustic matching layer 51. The acoustic matching layer 51 fits within a space between the first terminal array 33a and the second terminal array 33b. The edges of the acoustic matching layer 51 are spaced apart from the first side 21a and the second side 21b, respectively, of the base 21. The acoustic matching layer 51 has an outline that is smaller than the outline of the base 21.

The acoustic lens 18 is disposed on the acoustic matching layer 51. The acoustic lens 18 is in close contact with a surface of the acoustic matching layer 51. The acoustic matching layer 51 serves to allow the acoustic lens 18 to adhere to the base 21. The partial cylindrical surface 18a of the acoustic lens 18 has generating lines that are parallel to the first electric conductors 29. The curvature of the partial cylindrical surface 18a is determined in accordance with the focus position of ultrasonic waves emitted from a single row of elements 23 connected to a single second electric conductor 32. The acoustic lens 18 may be formed of, for example, a silicone resin. The acoustic lens 18 has an acoustic impedance that is similar to the acoustic impedance of a living body.

A protective film 53 is fixed to the base 21. The protective film 53 may be formed of a material that is impervious to water, such as an epoxy resin, for example. However, the protective film 53 may also be formed of other resin materials. The protective film 53 is fixed to side surfaces of the acoustic lens 18 and the acoustic matching layer 51. The protective film 53 overlaps the second electric conductors 32 and the extraction interconnects 31 on the surface of the base 21 in regions between the acoustic matching layer 51 and the first and second wiring boards 38 and 41. Similarly, the protective film 53 overlaps end portions of the first wiring board 38 and the second wiring board 41 on the base 21.

A backing material 54 is fixed to the back surface of the base 21. The back surface of the base 21 is superposed on a surface of the backing material 54. The backing material 54 closes the openings 46 in the back surface of the ultrasonic device 17. The backing material 54 can be provided with a rigid base material. Herein, the partitioning walls 47 are coupled to the backing material 54 at their joint surfaces 47a. The backing material 54 is joined to each partitioning wall 47 in at least one joint region. An adhesive can be used to join the backing material 54 to the partitioning walls 47.

Figure 4:
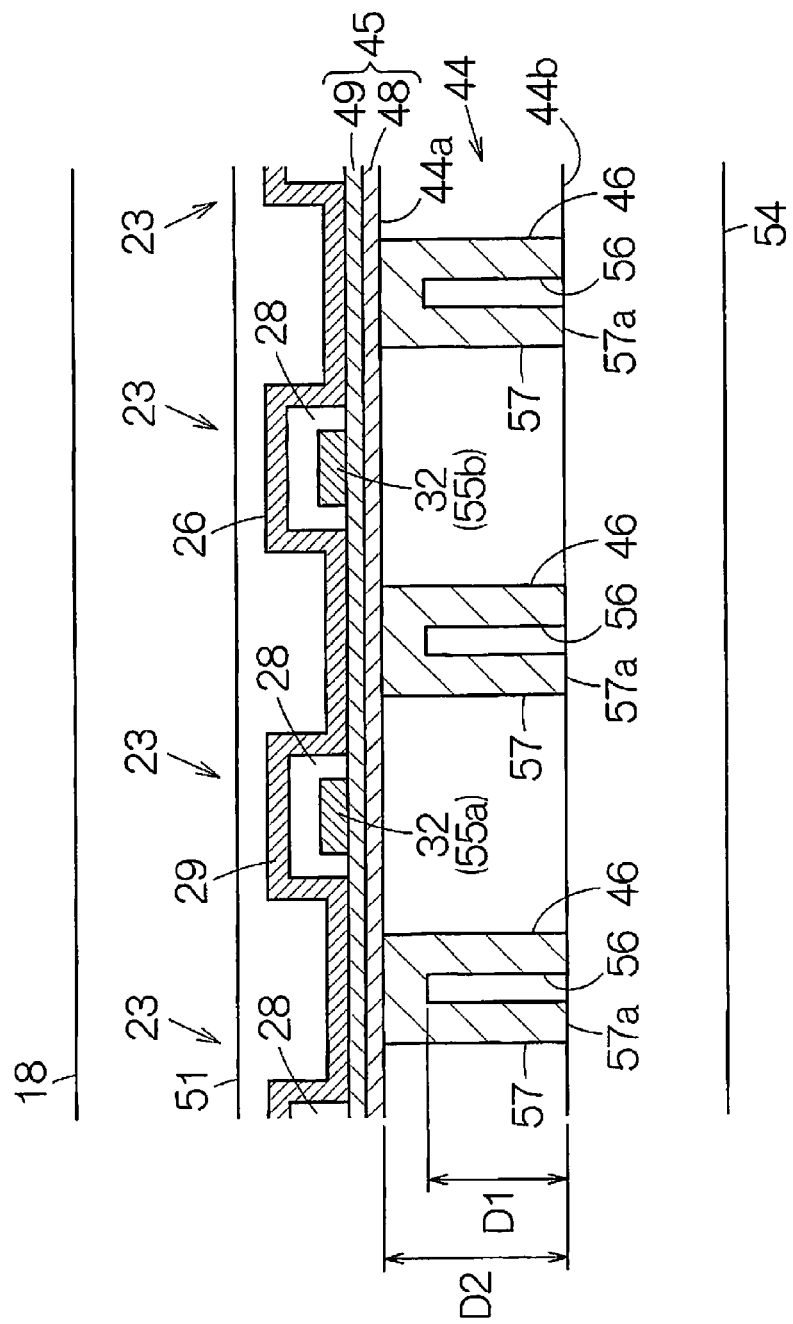
FIG. 4 is a partial enlarged cross-sectional view of the ultrasonic device taken along line B-B in FIG. 3.

As shown in FIG. 4, in a scanning direction of the ultrasonic device unit DV, each first electric conductor 29 is connected commonly to the piezoelectric films 28 of a plurality of elements 23. In a slice direction of the ultrasonic device unit DV, each second electric conductor 32 is connected commonly to the piezoelectric films 28 of a plurality of elements 23 belonging to a single group, such as a first group, a second group, and an n-th group. The second electric conductors 32 are isolated from one another by an insulator and form a first interconnect 55a, a second interconnect 55b, . . . , and an n-th interconnect, respectively. Signals are separately transmitted through the first interconnect 55a, the second interconnect 55b, . . . , and the n-th interconnect. The openings 46 of the first group, the openings 46 of the second group, . . . , and the openings 46 of the n-th group are isolated from one another by partitioning walls 57. The partitioning walls 57 are coupled to the backing material 54 at their joint surfaces 57a. A space 56 is demarcated in each partitioning wall 57, where the space 56 is hollowed out from the back surface (joint surface 57a) of the substrate 44 and does not pass through the substrate 44. The space 56 constitutes a recess that opens in the back surface 44b of the substrate 44. Since the spaces 56 do not pass through the substrate 44, the depth D1 of the individual spaces 56 from the back surface 44b of the substrate 44 in a direction perpendicular to the back surface 44b is smaller than the depth D2 of the individual openings 46, which pass through the substrate 44. The depth D1 of the individual spaces 56 (recesses) refers to the distance from the back surface 44b of the substrate 44 to the bottom of the individual spaces 56.

Figure 5:
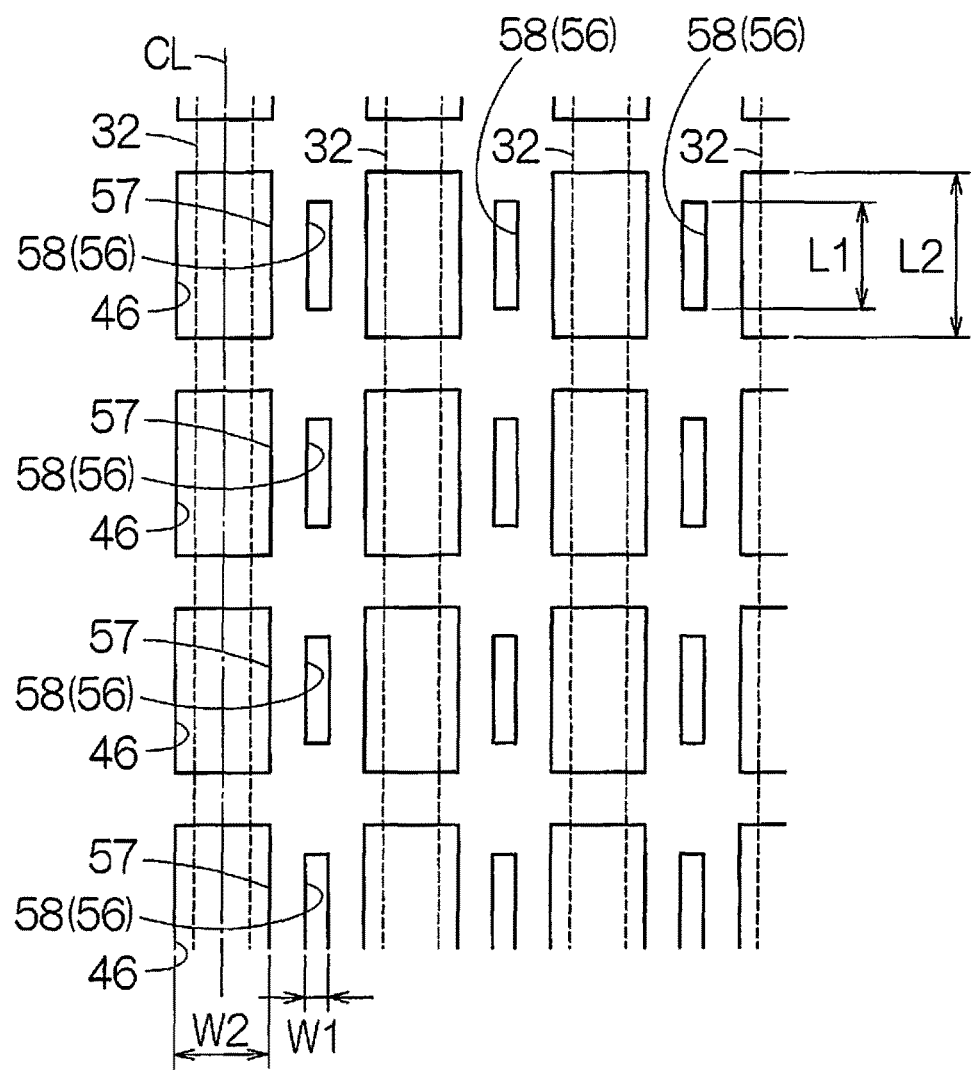
FIG. 5 is a partial enlarged plan view of the ultrasonic device when viewed from a back surface thereof.

As shown in FIG. 5, in a plan view when viewed in a thickness direction of the substrate 44, the spaces 56 are defined by respective grooves 58 extending in an extending direction of the partitioning walls 57, which isolate the openings 46 of the first group, the openings 46 of the second group, . . . , and the openings 46 of the n-th group from one another. The width W1 of the individual grooves 58 is smaller than the width W2 of the individual openings 46. For example, the "width" can be measured in a direction orthogonal to the center line CL of the second electric conductors 32 in the back surface of the substrate 44. In addition, in a plan view when viewed in the thickness direction of the substrate 44, the length L1 of the individual grooves 58 in the extending direction of the partitioning walls 57, which isolate the openings 46 of the first group, the openings 46 of the second group, . . . , and the openings 46 of the n-th group from one another, is smaller than the length L2 of the individual openings 46. For example, in the case where an extending direction of a row in which a first opening 46 and a third opening 46 are arranged is defined in the n-th group, an extending direction of a row in which a second opening 46 and a fourth opening 46 are arranged is defined in an (n+1)-th group. At this time, a first recess (groove 58) is formed in the partitioning wall 57 that separates the first opening 46 and the second opening 46 from each other, and a second recess (groove 58) is formed in the partitioning wall 57 that separates the third opening 46 and the fourth opening 46 from each other.

(3) Operation of Ultrasonic Diagnostic Apparatus

Next, the operation of the ultrasonic diagnostic apparatus 11 will be briefly described. To transmit ultrasonic waves, a pulse signal is supplied to the piezoelectric elements 25. The pulse signal is supplied to the elements 23 on a row-by-row basis through the bottom electrode terminals 35 and 37 and the top electrode terminals 34 and 36. In each of the elements 23, an electric field acts on the piezoelectric film 28 between the bottom electrode 27 and the top electrode 26. The piezoelectric film 28 vibrates at the frequency of ultrasonic waves. The vibration of the piezoelectric film 28 is transferred to the vibration film 24. Thus, the vibration film 24 vibrates ultrasonically. As a result, a desired ultrasonic beam is emitted toward the subject (for example, the interior of a human body).

Reflected waves of the ultrasonic waves vibrate the vibration film 24. The ultrasonic vibration of the vibration film 24 ultrasonically vibrates the piezoelectric film 28 at a desired frequency. A voltage is output from the piezoelectric element 25 in accordance with the piezoelectric effect of the piezoelectric element 25. In each of the elements 23, a potential is generated between the top electrode 26 and the bottom electrode 27. The generated potentials are output from the bottom electrode terminals 35 and 37 and the top electrode terminals 34 and 36 as electric signals. The ultrasonic waves are detected in this manner.

Ultrasonic waves are repeatedly transmitted and received. As a result, a linear scan or a sector scan is achieved. When the scan is completed, an image is formed based on digital signals of the output signals. The image thus formed is displayed on the screen of the display panel 15.

During the operation, the vibration films 24 of the ultrasonic device 17 vibrate. Since the spaces 56 are demarcated in the respective partitioning walls 57, vibration propagating through the partitioning walls 57 is reflected by the spaces 56. Accordingly, propagation of vibration from a vibrating vibration film 24 toward an adjacent vibration film 24 is suppressed. In this manner, crosstalk between adjacent vibration films 24 is reduced. At this time, since the spaces 56 do not pass through the substrate 44 and thus do not reach the surface 44a of the substrate 44, no groove or depression is formed in a region of the surface of the base 21 between adjacent vibration films 24. The stiffness of supporting points of the vibration films 24 is maintained. The vibration characteristics of the vibration films 24 are maintained. Variation in the vibration characteristics is suppressed.

As described above, the second electric conductors 32 are isolated from one another by an insulator and form the first interconnect 55a, the second interconnect 55b, . . . , and the n-th interconnect, respectively. Signals are separately transmitted through the first interconnect 55a, the second interconnect 55b, . . . , and the n-th interconnect. The first interconnect 55a, the second interconnect 55b, . . . , and the n-th interconnect form respective channels. Thus, the spaces 56 are arranged at least in regions between different channels. Crosstalk between the channels is thus reduced.

The ultrasonic device 17 has a plurality of openings 46 for each channel. The openings 46 are closed by the respective vibration films 24, and the piezoelectric elements 25 are fixed to the respective vibration films 24. That is to say, the openings 46, the vibration films 24, and the piezoelectric elements 25 belonging to the first group form a single channel. The first interconnect 55a is connected commonly to the plurality of piezoelectric elements 25. Similarly, the openings 46, the vibration films 24, and the piezoelectric elements 25 belonging to the second group form a single channel. The second interconnect 55b is connected commonly to the plurality of piezoelectric elements 25. In this manner, signals are enhanced on a channel-by-channel basis.

In a plan view when viewed in the thickness direction of the substrate 44, the spaces 56 are defined by the respective grooves 58 extending in the extending direction of the partitioning walls 57 that isolate the openings 46 of the first group from the openings 46 of the second group. The grooves 58 can efficiently block propagation of vibration between the openings 46 of the first group and the openings 46 of the second group. Moreover, the depth D1 of the individual grooves 58 is smaller than the depth D2 of the individual openings 46. The spaces 56 are thus located away from the surface of the base 21. The stiffness of the base 21 can be maintained. In addition, the width W1 of the individual grooves 58 is smaller than the width W2 of the individual openings 46. The grooves 58 and the openings 46 can be formed simultaneously by etching. It is more difficult for an etching solution to enter the grooves 58 than to enter the openings 46. As a result, if the grooves 58 are formed such that their width W1 is narrow, even when a traditional method for forming the openings 46 is followed, the grooves 58 that are shallower than the openings 46 can be formed by simply making a change in patterning. Furthermore, since the length L1 of the individual grooves 58 is smaller than the length L2 of the individual openings 46, a higher stiffness of the base 21 can be secured while reducing the crosstalk.

(4) Method for Manufacturing Ultrasonic Device

Figure 6:
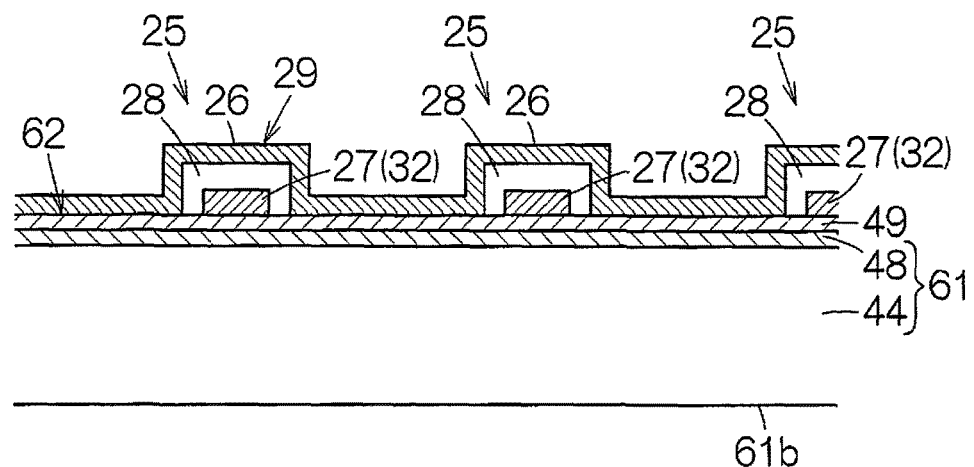
FIG. 6 is an enlarged cross-sectional view schematically showing steps up to formation of piezoelectric elements, of a method for manufacturing an ultrasonic device.

Next, a method for manufacturing the ultrasonic device 17 will be briefly described. As shown in FIG. 6, a substrate 61 is prepared. The substrate 61 may be formed of, for example, silicon. For example, heat treatment is applied to a surface (first surface) of the substrate 61, so that an oxide film is formed. The silicon of the substrate 61 is oxidized and forms silicon oxide. The oxide film has a uniform film thickness. In this manner, the substrate 44 and the silicon oxide layer 48 are formed from the substrate 61. The zirconium oxide layer 49 is formed over the entire surface of the silicon oxide layer 48. To form the zirconium oxide layer 49, a zirconium film having a uniform film thickness is laminated on the surface of the silicon oxide layer 48. To form the film, for example, sputtering may be used. Oxidation treatment is applied to the zirconium film. In this manner, the zirconium oxide layer 49 having a uniform film thickness is formed. A film member 62 is established by laminating the silicon oxide layer 48 and the zirconium oxide layer 49. The film member 62 corresponds to the coating film 45.

After that, the piezoelectric elements 25 are formed at predetermined positions on a surface of the film member 62. For example, a material layer made of an electrically conductive material is formed over the entire surface of the zirconium oxide layer 49. For example, sputtering may be used to form the material layer. The material layer is formed to have a uniform film thickness. A photoresist pattern is formed on the surface of the material layer. The pattern defines the shape of the second electric conductors 32. Etching is performed from the surface of the material layer. As a result, the second electric conductors 32 are formed from the material layer. Similarly, the piezoelectric films 28 and the top electrodes 26 (first electric conductors 29) are formed on the surface of the film member 62.

Figure 7:
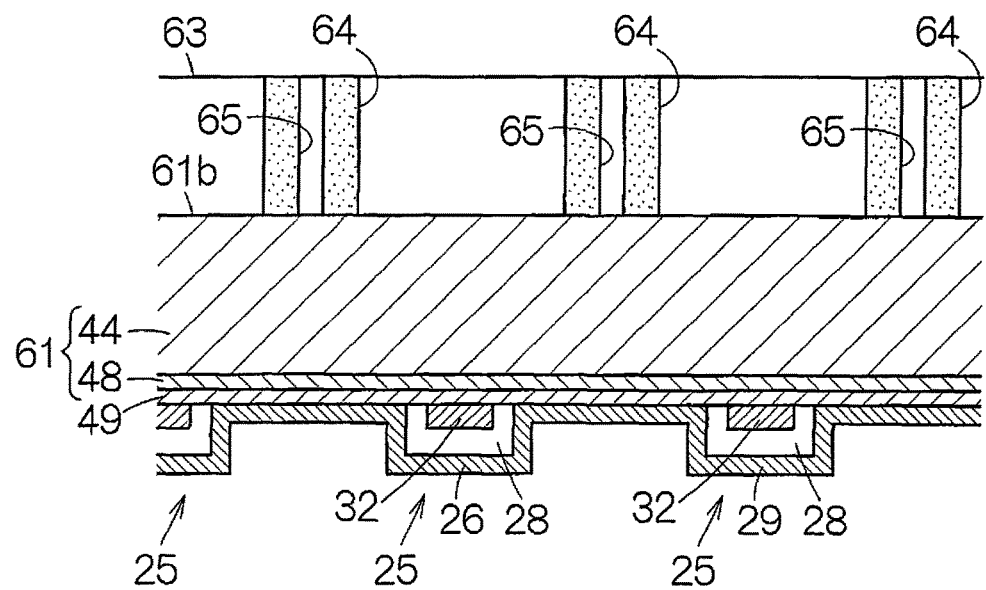
FIG. 7 is an enlarged cross-sectional view schematically showing a step of forming a resist film, of the method for manufacturing an ultrasonic device.

After the piezoelectric elements 25 as well as the first electric conductors 29, the second electric conductors 32, the top electrode terminals 34 and 36, and the bottom electrode terminals 35 and 37 are formed in the above-described manner, a resist film 63 is formed on a back surface (second surface) 61b of the substrate 61, as shown in FIG. 7. The resist film 63 may be formed of, for example, a photoresist material. The resist film 63 defines a predetermined pattern when viewed from above in the thickness direction of the substrate 61. The pattern demarcates large cavities 64 corresponding to the respective piezoelectric elements 25. The large cavities 64 respectively define the shapes of the outlines of the vibration films 24 on the back surface 61b of the substrate 61. Small cavities 65 are arranged between the large cavities 64 and define the shapes of the outlines of the grooves 58 on the back surface 61b of the substrate 61.

Figure 8:
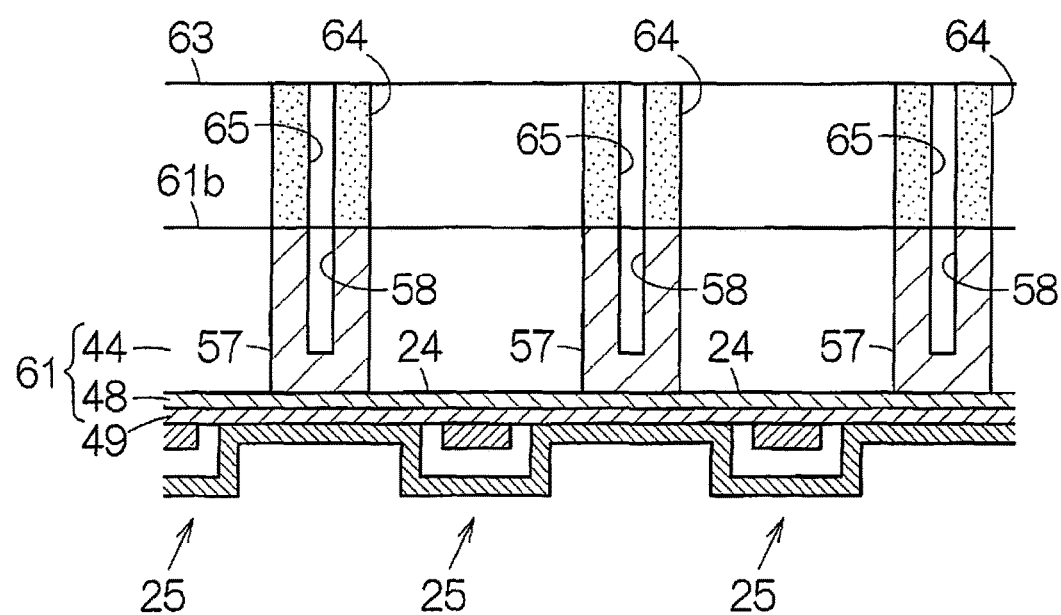
FIG. 8 is an enlarged cross-sectional view schematically showing a step of forming openings and grooves, of the method for manufacturing an ultrasonic device.

As shown in FIG. 8, the back surface 61b of the substrate 61 is subjected to an etching process. In accordance with the etching process, portions of the back surface 61b of the substrate 61 that are respectively located in the large cavities 64 and the small cavities 65 are engraved. When those portions of the substrate 61 that are respectively located in the large cavities 64 are engraved, and the resultant spaces reach the film member 62, the silicon oxide layer 48 functions as an etching stop layer. As a result, within the openings 46, the respective vibration films 24 are established in the film member 62. The partitioning walls 47 and 57 are formed between the openings 46.

At this time, those portions of the substrate 61 that are respectively located in the small cavities 65 are simultaneously engraved. The width of the individual small cavities 65 is smaller than the width of the individual large cavities 64, and therefore it is difficult for the etching solution to enter the small cavities 65. As a result, an etching rate that is smaller than that in the large cavities 64 is established in the small cavities 65. The small cavities 65 serve to allow the etching solution to make spaces in the substrate 61 from the back surface of the substrate 61 so that the resultant spaces have a depth D1 that is shallower than the depth D2 of the openings 46. In this manner, the spaces, namely, the grooves (recesses) 58 that do not pass through the substrate 61 are formed. Formation of the grooves 58 and formation of the openings 46 can be performed by the same etching process. Therefore, merely changing the patterning of the resist film 63 makes it possible to form the grooves 58 without increasing the manufacturing steps. The widths of the small cavities 65 and the large cavities 64 refer to the lengths thereof in the extending direction of the first electric conductors 29, which form a plurality of top electrodes 26.

(5) Ultrasonic Device According to Second Embodiment

Figure 9:
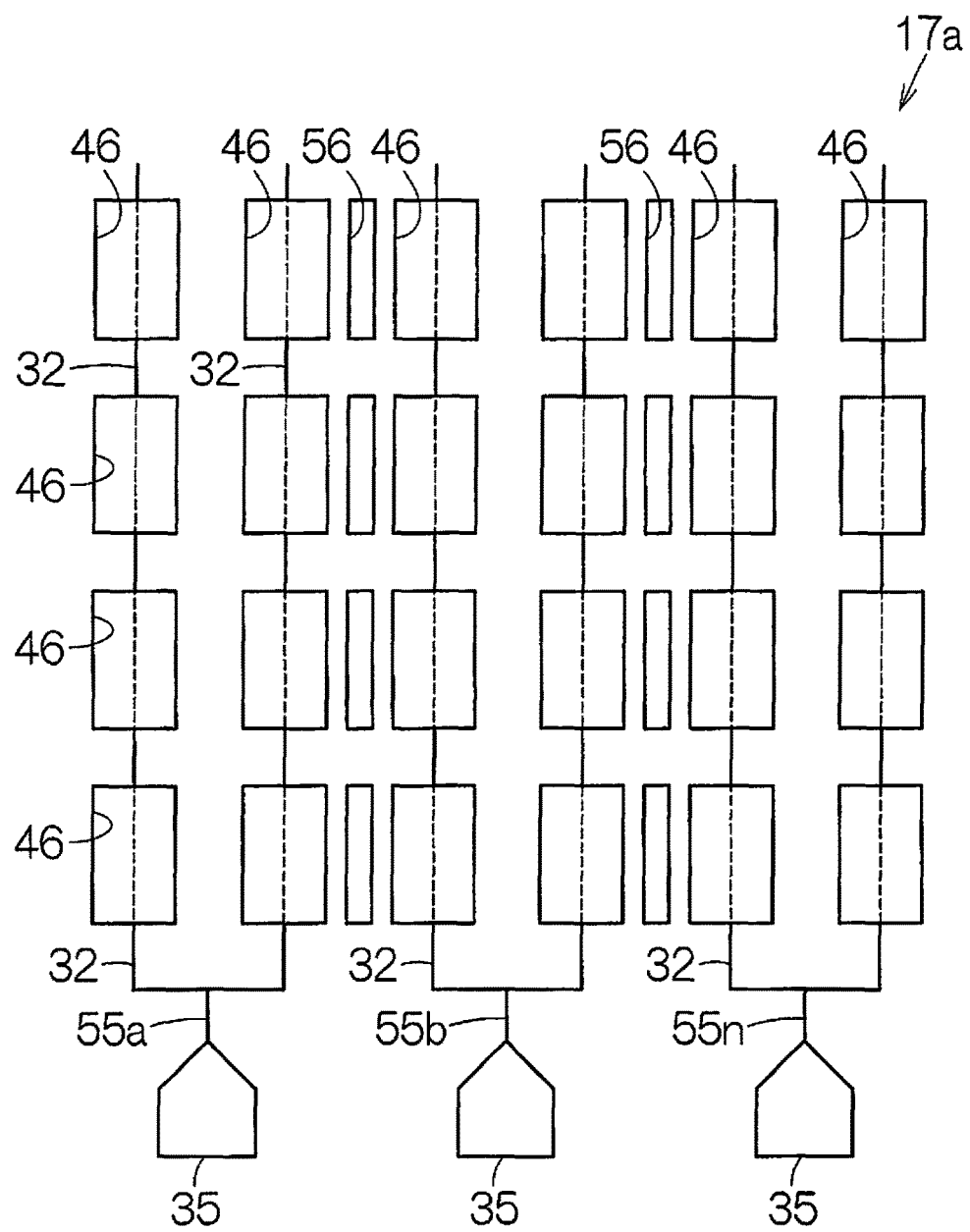
FIG. 9 is an enlarged conceptual plan view of an ultrasonic device according to a second embodiment.

FIG. 9 schematically shows the configuration of an ultrasonic device 17a according to a second embodiment. In this ultrasonic device 17a, the first interconnect 55a, the second interconnect 55b, . . . , and the n-th interconnect 55n are each formed by a plurality of second electric conductors 32. The openings 46 of the first group, the openings 46 of the second group, . . . , and the openings 46 of the n-th group are assigned to the first interconnect 55a, the second interconnect 55b, . . . , and the n-th interconnect 55n, respectively. The spaces 56 that are hollowed out from the back surface of the substrate 44 and that do not pass through the substrate 44 are demarcated in the partitioning walls 57 that isolate the openings 46 of the first group, the openings 46 of the second group, . . . , and the openings 46 of the n-th group from one another. Otherwise, the structure of the ultrasonic device 17a is the same as that of the ultrasonic device 17 according to the above-described first embodiment.

(6) Ultrasonic Device According to Third Embodiment

Figure 10:
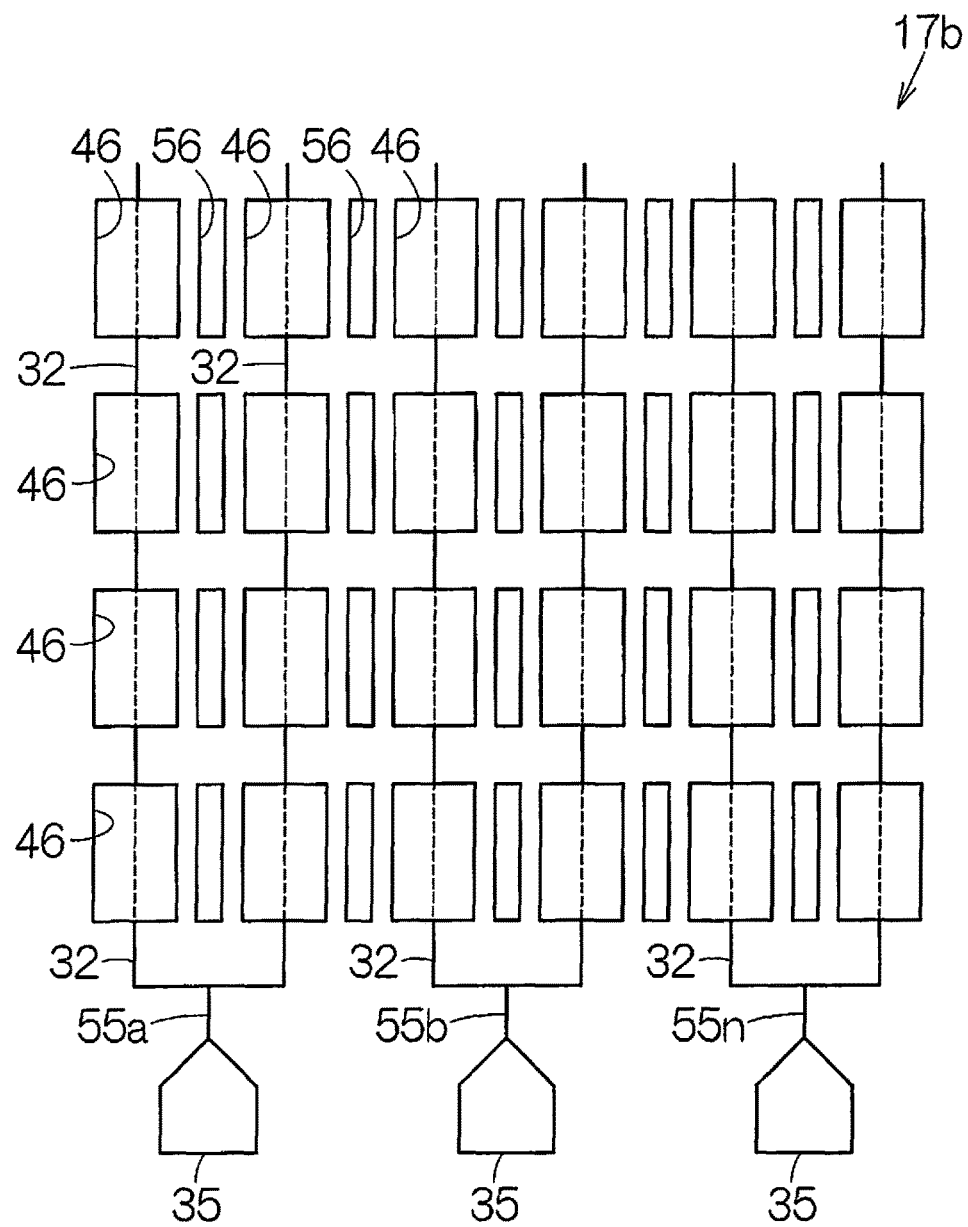
FIG. 10 is an enlarged conceptual plan view of an ultrasonic device according to a third embodiment.

FIG. 10 schematically shows the configuration of an ultrasonic device 17b according to a third embodiment. In this ultrasonic device 17b, as in the case of the second embodiment, the openings 46 of the first group, the openings 46 of the second group, . . . , and the openings 46 of the n-th group are assigned to the first interconnect 55a, the second interconnect 55b, . . . , and the n-th interconnect 55n, respectively. The spaces 56 that are hollowed out from the back surface of the substrate 44 and that do not pass through the substrate 44 are demarcated in not only the partitioning walls 57 that isolate the openings 46 of the first group, the openings 46 of the second group, . . . , and the openings 46 of the n-th group from one another but also the partitioning walls 57 that isolate the openings 46 assigned to a single second electric conductor 32 from the openings 46 assigned to another second electric conductor 32. Otherwise, the structure of the ultrasonic device 17b is the same as that of the ultrasonic device 17 according to the above-described first embodiment.

(7) Ultrasonic Device According to Fourth Embodiment

Figure 11:
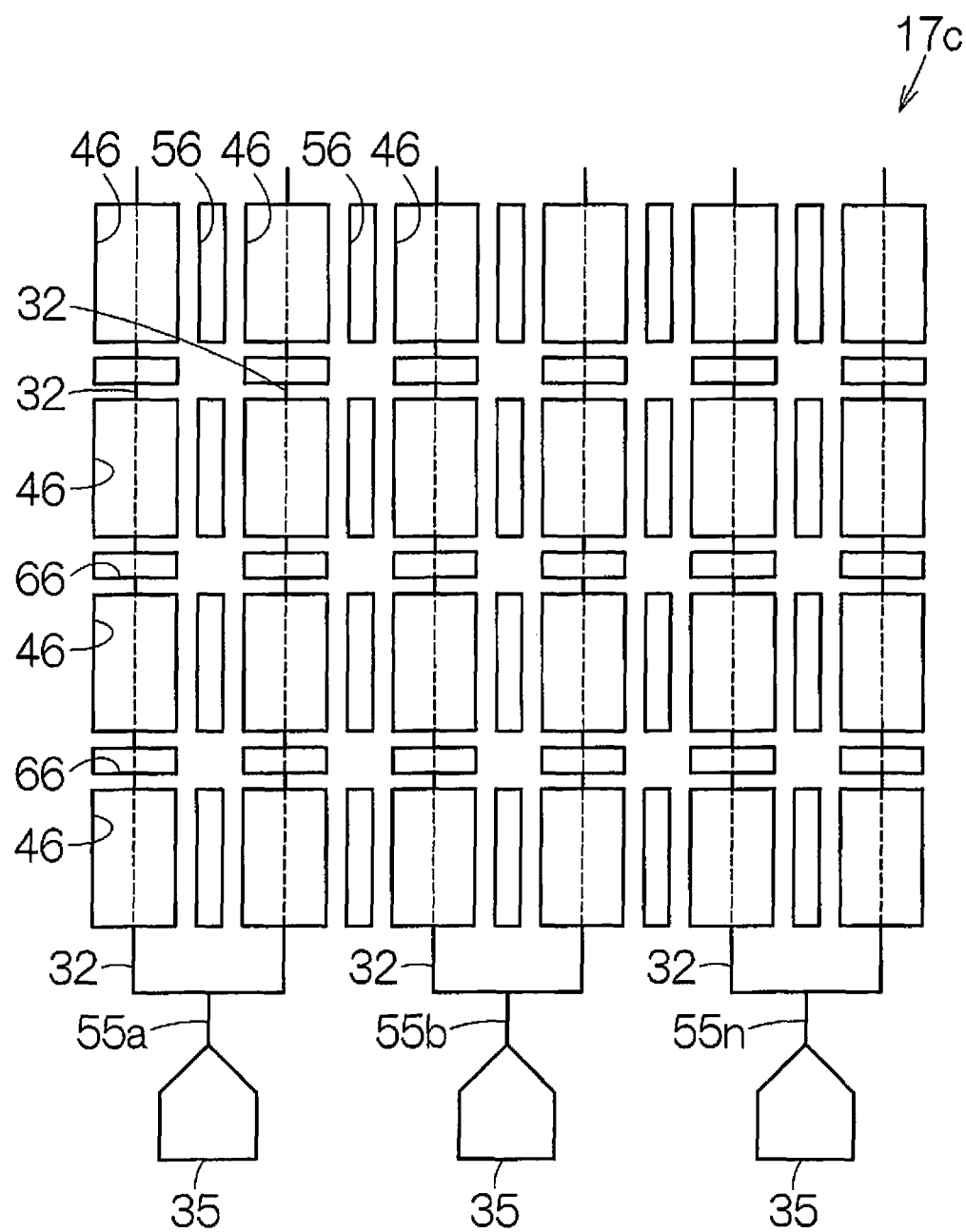
FIG. 11 is an enlarged conceptual plan view of an ultrasonic device according to a fourth embodiment.

FIG. 11 schematically shows the configuration of an ultrasonic device 17c according to a fourth embodiment. In this ultrasonic device 17c, as in the case of the third embodiment, the spaces 56 that are hollowed out from the back surface of the substrate 44 and that do not pass through the substrate 44 are demarcated in the respective partitioning walls 57 that isolate the openings 46 assigned to a single second electric conductor 32 from the openings 46 assigned to another second electric conductor 32. In addition, spaces 66 that are hollowed out from the back surface of the substrate 44 and that do not pass through the substrate 44 are demarcated in the respective partitioning walls 47 that isolate the openings 46 assigned to a single second electric conductor 32 from one another. The spaces 66 are defined by respective grooves extending in a direction that intersects the center line CL of the second electric conductors 32 at right angles. Otherwise, the structure of the ultrasonic device 17c is the same as that of the ultrasonic device 17 according to the above-described first embodiment. With this structure, propagation of vibration between the channels is blocked, and at the same time, within the same channel, propagation of vibration between the vibration films 24 is blocked.

(8) Ultrasonic Devices According to Fifth and Sixth Embodiments

Figure 12:
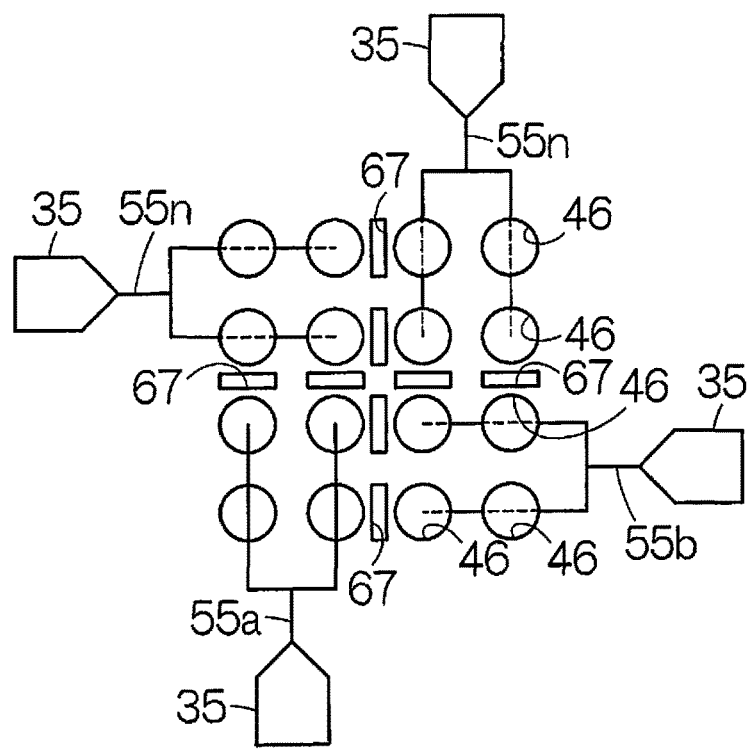
FIG. 12 is an enlarged conceptual plan view of an ultrasonic device according to a fifth embodiment.
Figure 13:
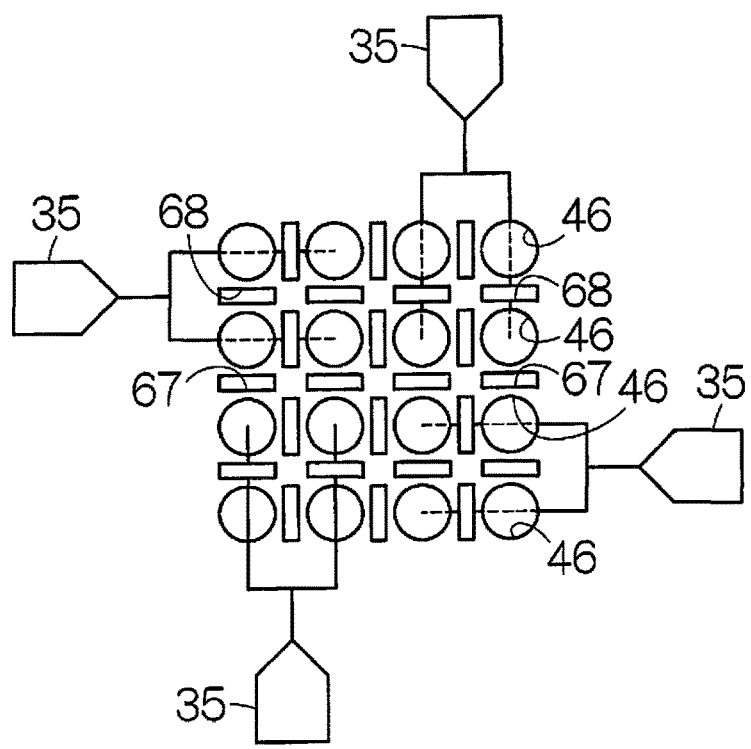
FIG. 13 is an enlarged conceptual plan view of an ultrasonic device according to a sixth embodiment.

Furthermore, the invention is not limited to a configuration in which the channels are arranged one-dimensionally as described in the first to fourth embodiments, and the channels may be arranged two-dimensionally as shown in, for example, FIGS. 12 and 13. In this case, as shown in FIG. 12, spaces 67 may be demarcated in the respective partitioning walls 57 between the channels, or as shown in FIG. 13, spaces 67 and 68 may be demarcated in the respective partitioning walls 47 and 57 that isolate the openings 46 from one another both inside and outside the channels.

(9) Ultrasonic Device Unit According to Another Embodiment

Figure 14:
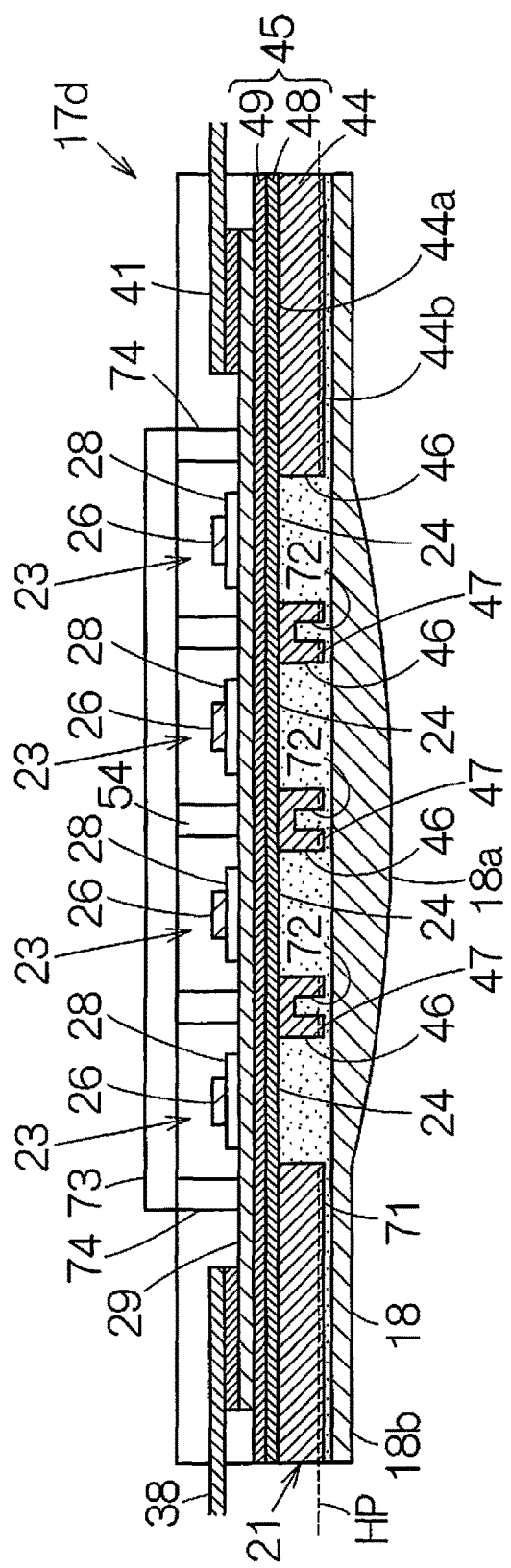
FIG. 14 is a partial cross-sectional view corresponding to FIG. 3 and showing an ultrasonic device unit according to another embodiment.

FIG. 14 schematically shows the configuration of an ultrasonic device unit DVa according to another embodiment. In the ultrasonic device unit DVa, the acoustic lens 18 is coupled to the back surface (second surface) 44b of the substrate 44. To couple the acoustic lens 18 to the back surface 44b of the substrate 44, an acoustic matching layer 71 is laminated on the back surface 44b of the substrate 44. The acoustic matching layer 71 covers the back surface of the substrate 44 and is also disposed within the openings 46. The acoustic matching layer 71 is in contact with the vibration films 24 within the respective openings 46. The acoustic matching layer 71 is in close contact with each vibration film 24 while leaving no space therebetween. For example, a silicone resin film may be used for the acoustic matching layer 71. The acoustic lens 18 is laminated on the acoustic matching layer 71. The acoustic lens 18 is in close contact with a surface of the acoustic matching layer 71 while leaving no space therebetween.

In the same manner as described above, the partitioning walls 47 and 57 are formed between the openings 46. Spaces 72 that are hollowed out from the back surface 44b of the substrate 44 and that do not pass through the substrate 44 can be formed in the partitioning walls 47 and 57. It is also possible that the spaces 72 are formed in only the partitioning walls 57 as described above. It is sufficient if the spaces 72 are the grooves. The acoustic matching layer 71 can be disposed within the spaces 72. The acoustic matching layer 71 and the substrate 44 have mutually different acoustic impedances, and thus vibration is reflected by an interface between the acoustic matching layer 71 and the substrate 44. In this manner, propagation of vibration is blocked.

On the surface of the substrate 44, a backing material 73 is attached onto the coating film 45. The backing material 73 forms a space between the backing material 73 and a surface of the coating film 45. The piezoelectric elements 25 are arranged within that space. The backing material 73 is supported on the surface of the coating film 45 via wall materials 74. The wall materials 74 maintain a certain distance between the backing material 73 and the surface of the coating film 45. The wall materials 74 are supported on the substrate 44 outside the outlines of the respective openings 46.

Although some embodiments of the invention have been described in detail above, a person skilled in the art will readily understand that various modifications may be made without substantially departing from the novel teachings and the effects of the invention. Therefore, such modifications are entirely included within the scope of the invention. For example, any term described at least once together with a broader or synonymous different term in the specification or the drawings may be replaced by the different term at any place in the specification or the drawings. Moreover, the configurations and operations of the device terminal 12, the ultrasonic probe 13, the housing 16, the display panel 15, and the like are not limited to those described in the foregoing embodiments, but may be modified in various manners.

The entire disclosure of Japanese Patent Application No. 2014-156708 filed on Jul. 31, 2014 is expressly incorporated by reference herein.

What is claimed is:

1. An ultrasonic device, comprising:
a substrate having a first surface and a second surface on a side opposite to the first surface in a thickness direction of the substrate and defining a first opening demarcated by a first wall portion that is disposed adjacent to the first opening;
a first vibration film that is disposed on the first surface of the substrate and that closes the first opening; and
a first piezoelectric element that is provided on the first vibration film,
wherein the first wall portion defines a first recess that opens in the second surface with a depth direction of the first recess extending along the thickness direction of the substrate.

2. The ultrasonic device according to claim 1,
wherein the substrate has a second opening that is separated from the first opening by the first wall portion,
the ultrasonic device further comprising:
a second vibration film that is deposed on the first surface of the substrate and that closes the second opening;
a second piezoelectric element that is provided on the second vibration film; and
a first interconnect that is connected to the first piezoelectric element and a second interconnect that is isolated from the first interconnect by an insulator and that is connected to the second piezoelectric element.

3. The ultrasonic device according to claim 2,
wherein the substrate has a third opening that is separated from the first opening by a second wall portion and a fourth opening that is separated from the second opening by a third wall portion and separated from the third opening by a fourth wall portion,
the ultrasonic device further comprising:
a third vibration film and a fourth vibration film that are disposed on the first surface of the substrate and that close the third opening and the fourth opening, respectively; and
a third piezoelectric element and a fourth piezoelectric element that are provided on the third vibration film and the fourth vibration film, respectively,
the third piezoelectric element being connected to the first interconnect and the fourth piezoelectric element being connected to the second interconnect, and
a second recess that opens in the second surface being formed in the fourth wall portion.

4. The ultrasonic device according to claim 3,
wherein the first recess and the second recess in a plan view when viewed in a thickness direction of the substrate are groove-shaped, extending in an extending direction of a row in which the first opening and the third opening are arranged.

5. The ultrasonic device according to claim 4,
wherein the first recess and the second recess have a depth that is smaller than depths of all of the first to fourth openings.

6. The ultrasonic device according to claim 5,
wherein a width of the first recess and a width of the second recess in a direction that crosses the extending direction of the row in which the first opening and the third opening are arranged are smaller than widths of all of the first to fourth openings.

7. The ultrasonic device according to claim 4,
wherein with respect to the extending direction, the first recess and the second recess have a length that is smaller than lengths of all of the first to fourth openings.

8. The ultrasonic device according to claim 3,
wherein a third recess that opens in the second surface is formed in the second wall portion, and a fourth recess that opens in the second surface is formed in the third wall portion.

9. The ultrasonic device according to claim 8,
wherein the third recess and the fourth recess are groove-shaped, respectively extending in a direction that intersects the first interconnect that connects the first piezoelectric element and the third piezoelectric element and a direction that intersects the second interconnect that connects the second piezoelectric element and the fourth piezoelectric element.

10. A probe, comprising:
the ultrasonic device according to claim 1; and
a housing that supports the ultrasonic device.

11. An electronic apparatus, comprising:
the ultrasonic device according to claim 1; and
a processor that is connected to the ultrasonic device and that processes an output from the ultrasonic device.

12. An ultrasonic imaging apparatus, comprising:
the ultrasonic device according to claim 1; and
a display device that displays an image generated based on an output from the ultrasonic device.

\* \* \* \* \*